United States Patent [19]

Frazier

[11] Patent Number: 4,604,110
[45] Date of Patent: Aug. 5, 1986

[54] FILTER ELEMENT, FILTER, AND METHOD FOR REMOVING ODORS FROM INDOOR AIR

[75] Inventor: Stephen E. Frazier, Orlando, Fla.

[73] Assignee: General Time Corporation, Norcross, Ga.

[21] Appl. No.: 707,119

[22] Filed: Feb. 28, 1985

Related U.S. Application Data

[63] Continuation-in-part of Ser. No. 601,946, Apr. 19, 1984, Pat. No. 4,534,775, which is a continuation of Ser. No. 354,030, Mar. 2, 1982, abandoned.

[51] Int. Cl.[4] .............................. B01D 53/04
[52] U.S. Cl. .............................. 55/74; 55/75; 55/385 R; 55/387; 55/389; 55/471; 55/518; 55/524; 422/122
[58] Field of Search .............. 55/73, 75, 279, 316, 55/385 R, 387, 389, 471–473, 516, 518, 519, 524; 162/160, 161; 210/501, 502; 422/120, 122; 424/195

[56] References Cited

U.S. PATENT DOCUMENTS

| | | | |
|---|---|---|---|
| 1,737,532 | 11/1929 | Allen | 55/387 |
| 1,789,194 | 1/1931 | Rockwell | 422/122 X |
| 1,801,506 | 4/1931 | Jenks | 55/316 |
| 1,972,368 | 9/1934 | Alex | 55/387 |
| 2,055,774 | 9/1936 | Ray | 55/387 |
| 2,362,933 | 11/1944 | Schaefer | 55/387 |
| 2,394,887 | 2/1946 | Berl | 422/122 X |
| 2,765,046 | 10/1956 | Rondholz | 55/279 X |
| 2,798,718 | 7/1957 | Gross | 55/316 X |
| 2,882,244 | 4/1959 | Milton | 55/75 X |
| 2,920,050 | 1/1960 | Blacet et al. | 422/122 X |
| 2,920,051 | 1/1960 | Wiig et al. | 422/122 X |
| 3,006,153 | 10/1961 | Cook | 55/389 X |
| 3,017,239 | 1/1962 | Rodman | 55/279 X |
| 3,029,581 | 4/1962 | Robbins | 55/316 |
| 3,049,399 | 8/1962 | Gamson et al. | 55/387 X |
| 3,091,550 | 5/1963 | Doying | 55/389 X |
| 3,116,969 | 1/1964 | Coleman, Jr. | 55/279 X |
| 3,138,432 | 6/1964 | Kleinhans | 422/122 |
| 3,200,569 | 8/1965 | Wheeler | 55/208 |
| 3,221,477 | 12/1965 | Arnoldi et al. | 55/31 |
| 3,226,332 | 12/1965 | Lincoln et al. | 252/184 |
| 3,325,402 | 6/1967 | Erskine | 210/501 X |
| 3,359,707 | 12/1967 | Jean | 55/33 |
| 3,381,454 | 5/1968 | Sponsel | 55/528 |
| 3,457,040 | 7/1969 | Jennings | 422/122 X |
| 3,526,322 | 9/1970 | Burroughs et al. | 55/389 X |
| 3,528,224 | 9/1970 | Warn | 55/179 |
| 3,555,787 | 1/1971 | Lustig | 55/179 |
| 3,557,534 | 1/1971 | Kennedy | 55/75 |
| 3,589,106 | 6/1971 | Onuki | 55/279 |
| 3,658,467 | 4/1972 | Maeck | 55/75 X |
| 3,672,126 | 6/1972 | Goettle | 55/316 |
| 3,683,596 | 8/1972 | Ashley | 55/389 X |
| 3,757,495 | 9/1973 | Sievers | 55/316 X |
| 3,844,787 | 10/1974 | Macriss et al. | 55/75 X |
| 3,892,549 | 7/1975 | Lyshkow | 55/316 X |
| 3,906,798 | 9/1975 | Dray | 55/316 X |
| 3,941,573 | 3/1976 | Chapel | 55/389 X |
| 3,966,442 | 6/1976 | Waters | 55/316 |
| 4,012,206 | 3/1977 | Macriss et al. | 55/75 X |
| 4,021,577 | 5/1977 | Harich et al. | 424/195 |
| 4,064,876 | 12/1977 | Mulchi | 55/316 X |
| 4,146,566 | 3/1979 | Gaiser | 422/122 |
| 4,239,516 | 12/1980 | Klein | 55/389 |
| 4,337,276 | 6/1982 | Nakamura et al. | 55/389 X |
| 4,343,765 | 8/1982 | Elston et al. | 422/122 X |
| 4,459,269 | 7/1984 | Zackey et al. | 423/219 |
| 4,474,739 | 10/1984 | Zackey et al. | 423/230 |
| 4,534,775 | 8/1985 | Frazier | 55/389 X |

FOREIGN PATENT DOCUMENTS

109069  8/1979  Japan ........................ 422/122

Primary Examiner—Robert Spitzer
Attorney, Agent, or Firm—Pennie & Edmonds

[57] ABSTRACT

An air filter element for removing odors from indoor air having a dry of a mixture of silica gel, activated carbon, and a zeolite. This dry mixture may also be impregnated with a liquid for inhibiting the growth of microorganisms, the liquid being a fungicide/bacteriocide preservative and a polyhydric alcohol, or a grapefruit pulp-/polyhydric alcohol reaction product. Also disclosed are novel air filters having these air filter elements and a material for removing particulate matter from indoor air.

42 Claims, 7 Drawing Figures

FILTER ELEMENT, FILTER, AND METHOD FOR REMOVING ODORS FROM INDOOR AIR

CROSS REFERENCE TO RELATED APPLICATIONS

This application is a continuation-in-part of application Ser. No. 601,946, filed Apr. 19, 1984, now U.S. Pat. No. 4,534,775, which is a continuation of application Ser. No. 354,030 filed Mar. 2, 1982, abandoned.

TECHNICAL FIELD

The present invention relates to air treatment filter elements and air treatment filters. Specifically, the invention relates to air filter elements, filters, and methods for removing odors from indoor air.

BACKGROUND OF THE INVENTION

There are a number of methods and apparatus for treating indoor air. Such air normally contains odors and particulate matter and various systems have attempted to control both problems.

Filtration is generally considered to be the separation of particles or solids from a heterogeneous mixture of a fluid, such as air. These solids or particles are removed from the air by forcing the air through a filter medium, or septum, upon which the solids are deposited.

It is well known that dust can be removed from the air by filters, electrostatic precipitation, washing of the air with a water spray, or dynamic precipitation. The first method, filtration, has been the most efficient and effective procedure for the removal of dust from indoor air. In general, air filters are used where the dust concentration is relatively low and does not exceed 4 g. per 1,000 cu. ft. of air. The filtering medium varies, and glass fibers, wire screen, steel wool, animal hair and hemp fibers have all been employed.

In addition to dust, indoor air contains numerous odorous pollutants, including formaldehyde, acetic acid, ammonia, hydrogen sulfide, sulfur dioxide and solvent gases such as benzene and toluene. Furthermore, such air often contains additional odors such as bathroom odors, kitchen odors, basement odors, tobacco odors and the like.

The most common method for removing these odors is ventilation or the supply of fresh air to and the removal of contaminated air from a space or room. Under very cold or very hot climatic conditions, ventilation is not desirable for obvious reasons.

Other methods exist for "masking" odors in indoor air by covering such odors with a fragrance or other pleasant-smelling material. These methods, however, do not remove the offensive odors from indoor air, but merely disguise them as non-offensive odors.

According to the prior art, indoor air treatment systems for the removal of odors have employed special liquids for the removal of odors as well as for inhibiting the growth of microorganisms, many of which are odor causing by themselves. While these air treatment systems have been effective to deodorize, such systems have been complex and expensive to operate, and lack both high capacity and high efficiency for removing a broad spectrum of pollutants including formaldehyde and other solvent gases, from indoor air.

Other specialized air purification systems have attempted to remove odors. The only practical method disclosed by the prior art of removing odors from air is by active carbon adsorption and this has been found useful against cooking, body and tobacco odors. While effective initially, active carbon loses its effectiveness over time, and also is not useful for removing the broad spectrum of odors generally encountered in a household environment.

Bacteria in the air stream presents another problem which requires the use of ultraviolet radiation or germicidal sprays for its removal. This technique, however, does not remove odors or particulate matter.

Thus, none of the prior art filters or filter elements are effective for the removal of a wide variety of odors and particulate matter from indoor air.

The present invention is directed to what can be termed air sanitation, the cleaning of air, whether the contaminating substance be dust, odors, fumes, or bacteria, and the applicant has surprisingly discovered combinations of dry or impregnated filter elements which provide increased deodorizing effectiveness or removal of a wide variety of odors and particulate matter from indoor air.

SUMMARY OF THE INVENTION

The present invention relates to an air filter element for removing odors from indoor air consisting essentially of a mixture of silica gel, activated carbon and a zeolite. This mixture comprises from about 10 to 80 weight percent of silica gel, from about 10 to 80 weight percent activated carbon, and from about 10 to 80 weight percent zeolite. Preferably, the amounts of silica gel, activated carbon, and zeolite are essentially equal.

The mixture can also contain a liquid for inhibiting the growth of microorganisms. This liquid comprises either a fungicide/bacteriocide preservative composition in an amount from about 0.5 to 2% by weight of the liquid, at least one polyhydric alcohol, said polyhydric alcohol being present in an amount from about 83 to 99.5% by weight of the liquid, and at least one additional compound for modifying the vapor pressure of said polyhydric alcohol or the product obtained by contacting grapefruit pulp with a non-toxic polyhydric alcohol to form a reaction product, and separating said reaction product from the pulp residue. The additional compound can be present in an amount from about 0 to 15% by weight of the liquid, and the liquid is present in an amount from about 5 to about 50% by weight of the combined weight of the mixture and the liquid. A preferred zeolite is zeolite X and a preferred polyhydric alcohol is propylene glycol.

The fungicide/bacteriocide preservative composition is in the liquid is captan, quaternary ammonium cosmetic preservatives, parabens, or iodophors. The fungicide/bacteriocide preservative composition should be present in an amount of about 1% by weight of the liquid, for best results.

For certain applications, the liquid can also further include a naringen-iron chelate produced from the reaction of naringen in an amount from about 0.1 to 0.2% by weight of the liquid with an iron salt in an amount from about 0.01 to 0.10% by weight of the liquid.

An advantageous polyhydric alcohol is a combination of propylene glycol, glycerin and tripropylene glycol and the preferred additional compound is water or glycerine.

An alternate embodiment of the invention relates to an air filter element for removing odors from indoor air consisting essentially of a first layer of silica gel impregnated with one of the liquids for inhibiting the growth of microorganisms described above and a second layer of zeolite, active carbon, silica gel or mixtures thereof.

The weight of the silica gel in the first layer before impregnation with the liquid ranges from about 1:3 to 3:1 times the weight of the zeolite, active carbon, silica gel or mixtures thereof in the second layer. Preferably the weight of silica gel in the first layer before impregnation with the liquid is essentially equal to the amount of zeolite, active carbon, silica gel or mixtures thereof in the second layer.

The first and second layers can be separated, but are adjacent in either a vertical or horizontal direction.

The invention also includes an air filter element for removing odors and particulate matter from indoor air comprising a first layer of one of the air filter elements described above, and at least one layer of particulate removal means located adjacent to the first layer. Preferably the particulate removal means is paper, felt, fabric, fiberglass, or plastic foam. Two layers of particulate removal means, can be used, one layer located on each side of and adjacent to the first layer.

Advantageously, the plastic foam is polyurethane containing 20 pores per inch, and the paper is high efficiency air filter paper.

The invention also contemplates an air treatment filter for removing odors and particulate matter from indoor air comprising housing means, at least one of the filter elements described above, support means for holding the filter element within the housing means, and fan means for directing indoor air into the housing and through the filter element.

Finally, the invention also discloses a method for removing odors and particulate matter from indoor air which comprises directing the indoor air through at least one of the above-described in filters.

BRIEF DESCRIPTION OF THE DRAWINGS

Further benefits and advantages of the invention will become apparent from a consideration of the following description given with reference to the accompanying drawing figures wherein.

DESCRIPTION OF THE PREFERRED EMBODIMENTS

Reference will now be made in detail to the preferred embodiments of the invention which are illustrated in the drawing figures.

Figure 1:
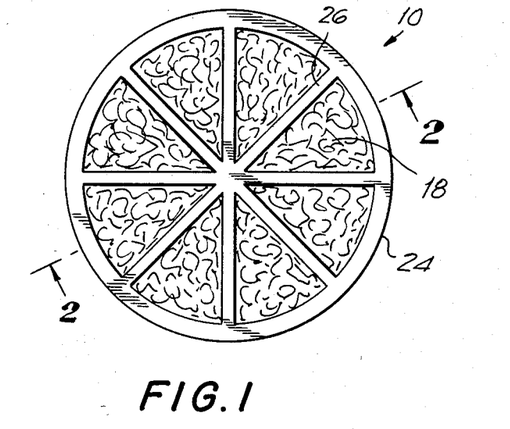
FIG. 1 is a top plan view of a filter element according to the invention.
Figure 2:
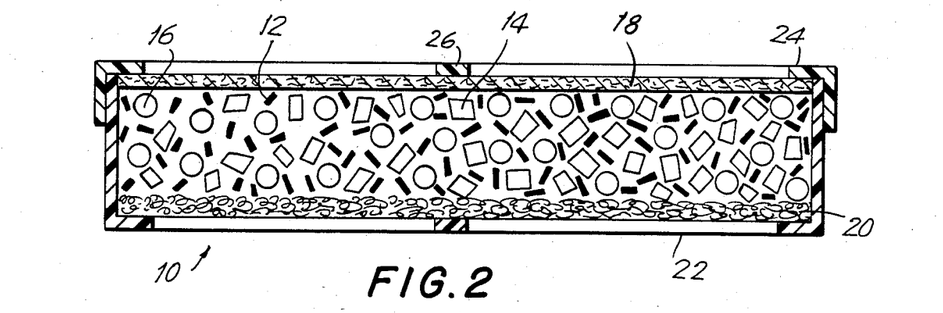
FIG. 2 is a cross-sectional view of the filter element of FIG. 1 taken along lines 2—2.

Referring initially to FIGS. 1 and 2, there is shown a filter element 10 according to the invention. This filter element 10 has, as the adsorbent media, a dry mixture of activated carbon 12, silica gel 14, and zeolite 16 particles. The mixture of particles is packed into the filter so as to minimize the pore volume or void space. This forces the air to contact the particles while passing through the filter so that air odors can be removed.

This filter element 10 also includes a top layer of high efficiency particulate removal paper 18, and a bottom layer of polyurethane foam 20. All these components are placed in a suitable two-piece plastic structure 22, 24. Preferable plastics for the construction of this structure include polystyrene or polypropylene. The structure also contains openings to allow for the passage of air.

In the manufacturing sequence, the filter element is constructed as follows. Into the bottom portion of the structure 22 is placed the polyurethane foam 20 or alternate particulate removal means. The dry mixture of adsorbent is then packed upon the foam 20. Then, the upper portion of the structure 24, which also contains the filter paper 18 or other particulate removal means, is closed over the lower structure. As one skilled in the art would realize, the top and bottom of the structures are designed so as to allow air flow through the filter element 10. Thus, as shown in FIG. 1, the structure is provided with ribs 26.

Figure 3:
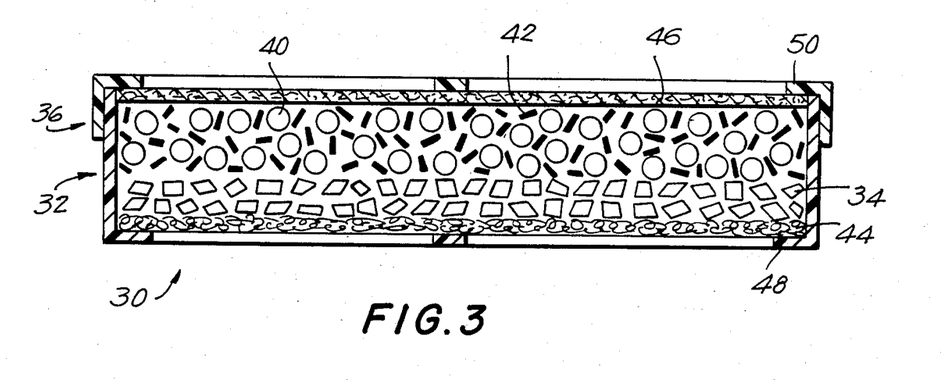
FIG. 3 is a cross-sectional view of a second filter element according to the invention.

In accordance with another embodiment of the invention and as shown in FIG. 3, an indoor air treatment filter element 30 comprises a first layer 32 of silica gel particles 34 containing the liquid (not shown) for inhibiting the growth of microorganisms. The liquid is present in the amounts previously described.

This filter element also contains a second layer 36 adjacent to the first layer 32, and includes a combination of zeolite spheres 40 and activated carbon 42. The zeolite and activated carbon can also contain silica gel as described above in the description of FIGS. 1 and 2. Optionally, the second layer can be impregnated with a liquid (not shown) for inhibiting the growth of microorganisms in the amounts previously described.

Further, the first and second layers, 32 and 36 respectively, are preferably positioned between two layers containing material for removing particulate matter from air. Any suitable material for removing particulate matter from air may be used in these layers. Preferably, in accordance withn the invention, the lower of these two layers 44 is a plastic foam such as polyurethane containing 20 pores per inch. The upper layer 46 is high efficiency particulate removal paper. Other particular filters include natural and synthetic fiber materials, including paper, cellulose and Filtret, a fiber filter mat manufactured by 3-M Company. Furthermore, the paper may be flat or corrugated, depending upon the size of the filter element and filter.

The air treatment filter element of FIG. 3 is also held within a two piece structure 48, 50, which is similar to that of FIG. 1. Again, any suitable material for holding the filter element while allowing air to pass through the filter element can be used. Preferably, the structure 48, 50 is made of a plastic such as polystyrene or polypropylene.

Figure 4:
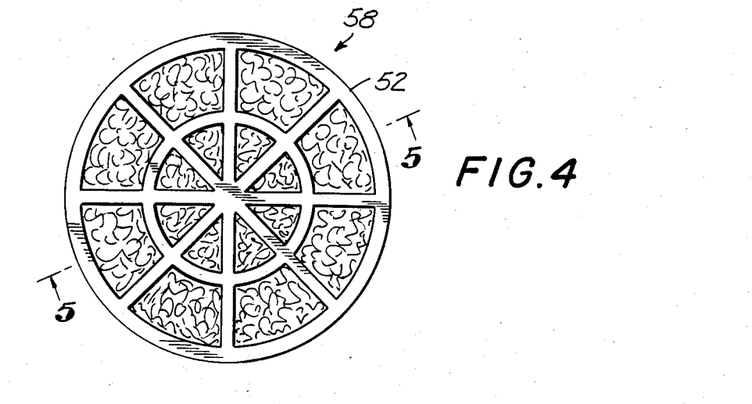
FIG. 4 is a top plan view of a third filter element according to the invention.
Figure 5:
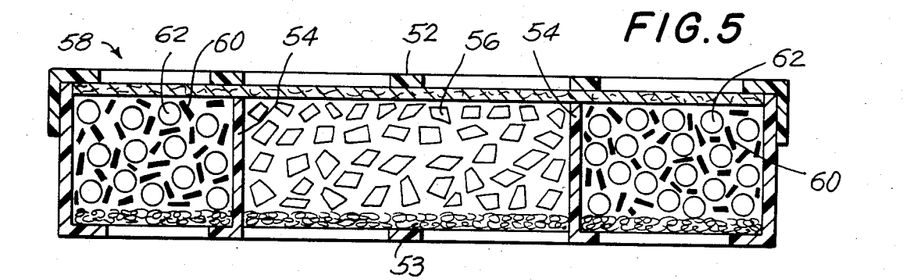
FIG. 5 is a cross-sectional view of the filter element of FIG. 4 taken along lines 5—5.

FIGS. 4 and 5 illustrate an alternate arrangement of the filter element 58 of the invention. In this arrangement, the structure 52, 53 for holding the adsorbent media is similar to that of FIG. 1, but further includes an inner wall 54 which forms two concentric compartments for separating the different adsorbent components. As shown, for example, the silica gel 56 can be placed in the center compartment, and the other adsorbent comprising a mixture of active carbon 60 and zeolite 62 can be placed in the outer compartment. The exact placement of the adsorbents is not critical, and it is just as feasible for the position of the adsorbents to be reversed. Also, other combinations of adsorbents can be used depending upon the particular odors to be removed from the indoor air.

Figure 6:
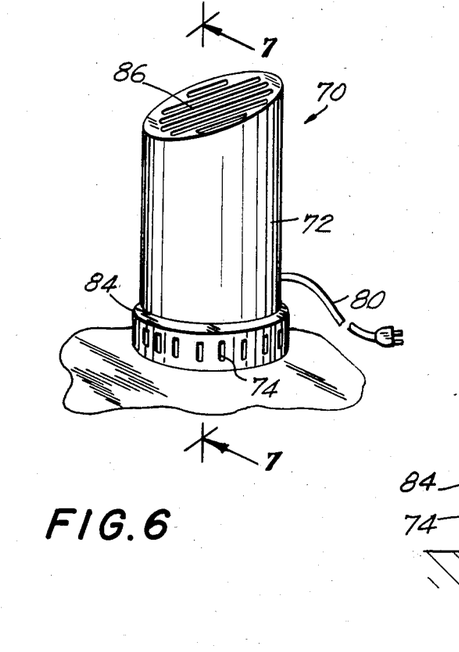
FIG. 6 is a side view of an indoor air filter according to the invention.
Figure 7:
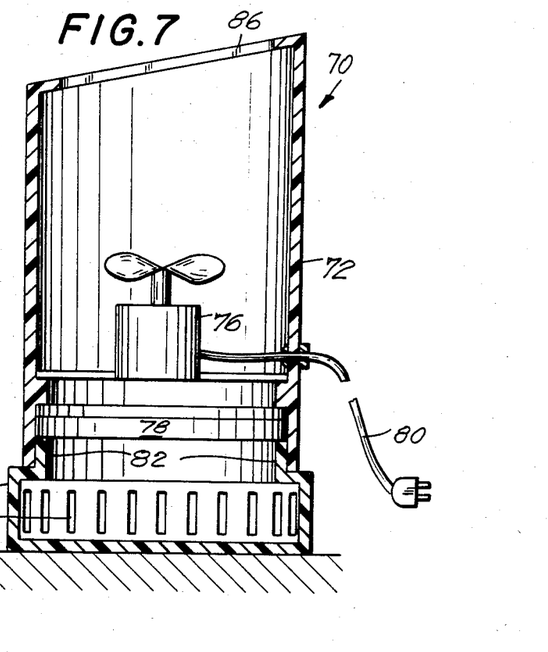
FIG. 7 is a cross-sectional side view of the indoor air filter of FIG. 6 taken along lines 7—7.

Referring now to FIGS. 6 and 7, there is illustrated a portable apparatus 70 for removing odors from indoor air. This apparatus 70 includes a housing 72 having openings 74 in the lower portion 84 for allowing the indoor air to enter into the unit. The fan also directs the cleaned air out of the unit through louvers 86 or holes in the top of the housing. The unit also includes a fan 76, blower or other air movement means for directing the air into the unit and for inducing air into the holes 74 and through the filter element 78. The fan 76 is suitably supported within the housing and is shown as being operated electrically with power cord 80. However, for some of the smaller units, it may be advantageous or desirable to operate the fan by a battery, and in that situation, suitable space is provided within the housing 72 for the fan, battery and necessary electrical connections (not shown).

The filter element 78 is as described previously, and is held within the housing by suitable supports 82. Since the filter element requires periodic replacement, the housing 72 is provided with a removable bottom 84 for access to the filter element 78. The housing 72 and bottom 84 can be constructed of a suitable plastic or metal material.

Although the apparatus is shown in the form of a portable unit, it is also within the scope of the invention to provide ductwork from a room or portion of the building which contains air to be deodorized, and to direct the air through the ductwork by suitable fan or blower means. Then, the ductwork is provided with one of the filter elements described above, and, after the air passes therethrough, the air is directed back into the room. For example, the filter elements of the present invention can be added to the ductwork of an indoor air conditioning system for removal of odors from the indoor air.

In accordance with the first embodiment of the invention, the air filter element includes an absorbent material consisting essentially of zeolite, activated carbon and silica gel. A zeolite is a natural hydrated silicate of aluminum and either sodium or calcium or both, of the type $Na_2OAl_2O_3nSiO_2xH_2O$. Molecular sieves belong to the class of minerals known as zeolites and the terms "molecular sieve" and "zeolite" can be used interchangeably. Because of the scarcity of natural zeolites and the high degree of chemical and physical variability inherent in the use of natural zeolites, workers have succeeded in synthesizing many pure zeolite species.

Commercially available artificial zeolites (molecular sieves) are useful in the present invention for absorbing odors from indoor air. Zeolite X is a preferred commercially available zeolite because it has pore sizes appropriate to absorb odors from gases such as formaldehyde, sulfur dioxide, hydrogen sulfide, benzene and toluene. Zeolite X is described in detail in U.S. Pat. No. 2,882,244, the disclosure of which is specifically incorporated herein by reference. A specifically preferred synthetic type X zeolite is 13-X, which is available commercially from the Linde Division of Union Carbide Corporation.

Activated carbon, a well-known commercially available material, is an amorphous form of carbon characterized by high absorptivity for many gases, vapors and colloidal solids. Any commercially available type of activated carbon is useful in the present invention.

The third component of the filter element is silica gel, a regenerative adsorbent consisting of amorphous silica. Silica gel is readily available commercially.

It is known that activated carbon can remove a variety of general odors from the air. It specifically is effective against non-polar compounds such as chlorinated hydrocarbons, aromatic compounds, and general organic compounds. Specifically, it is very effective against carbon tetrachloride, benzene, toluene and the like. Molecular sieves having a relatively small pore size are more effective against compounds such as hydrogen sulfide, alcohols, ester and aldehydes. Silica gel, which has larger pores in comparison to the molecular sieves and active carbon, is quite effective for long carbon chain compounds and specifically organic acids.

Applicant has found, however, that by combining these three ingredients into a single filter element, the removal capacity for a wide range of odors is provided. Also, the amount of odor removal is better than the sum total of each individual component. In addition, the applicant has found that aged filters i.e., those which have been standing for a significant length of time, perform much better for the removal of such gases and odors than the individual components themselves.

Originally, it was believed that individual layers of each component would be the most effective for removing all odors from indoor air. The reason for this belief was that since the indoor air would have to pass through each individual layer, the particular layer would remove the gases to which it was most effective and thus all odors would be removed from the air by this method. However, by increasing the number of layers and/or the thickness of each individual layer the pressure drop through the unit becomes significant. This requires higher volume fans or other means for inducing the air through the filter elements. Since these units are used for indoor air, and since almost all are portable, it is advantageous to make the fan means as small as possible, yet of sufficient capacity to achieve the desired results.

In this regard, it is also important to maintain the filter element in as thin a layer as will be effective for removing odors from the air. Depending on the size of the unit, the thickness of the filter may vary, however it is preferred that the filter be a maximum of about 2 inches thick. A typical thickness for the filters of the invention is about 0.5 inch. It is essential that the filters be completely full of the mixture of absorbents. No void spaces can be tolerated, because air can bypass the filter and thus carry odors which would not be removed back into the room. The filters are generally sized by the amount of volume of adsorbent, however, for simplicity in monitoring the proper amount of adsorbent in the filter, these volumes can be converted to weights.

The relative amount of each component in the dry mixture can be varied over a wide range depending upon the desired results. For example, if an indoor environment contains an unusually high amount of one particular odor, the component of the filter element which is most effective towards removing that odor can be increased. For example, for removal of hydrogen sulfide, it is advantageous to use a greater amount of zeolite in the mixture. Based on the known removal preferences for each absorbent, one skilled in the art could easily determine the optimum mixture for a specific odor removal situation.

It has also been found, however, that a minimum amount of each component should be present to obtain the advantageous removal rates according to the invention. In this regard, at least 10 weight percent of each of the component should be present. Therefore, the maximum concentration of any one component would be about 80 weight percent.

Two factors should be considered when attempting to remove odors from indoor air: first is the ability of the mixture to absorb the particular gases encountered and second is the quantity of the mixture. The first consideration relates to the proportions of each component in the mixture, while the second relates to the capacity or size of the filter. Since in ordinary situations, a wide variety of gases can be encountered, it is best to use equal amounts of each component. Then, depending upon the size of the unit, the amount of air to be cleaned, and the desired replacement time for the filter, the size or capacity of the filter can be selected. As mentioned above, the size of the filter also controls the size of the air moving means which in turn determines the energy requirements for the air filter.

The above described adsorbent mixtures are also effective for removing some particulate matter from the air. However, for specific particulate removal, high efficiency paper or polyurethane foam is preferred. These particulate removal materials should be present on at least one side of the filter element. In certain situations and areas where heavy particulate matter is to be encountered, i.e., extremely dusty areas, two layers of paper or foam, one on each side of the filter element, is preferred. Also, where various sizes of particular matter is encountered a common procedure is to use plastic foam on one side of the filter element and high efficiency particulate removal paper on the other side.

The dry absorbent mixture is preferably held in a plastic structure. However, it is also possible to utilize the paper and/or plastic foam in conjunction with a plastic support to hold the absorbent in position in the filter.

The mesh size of each component is not particularly critical, although it is preferable to have particle rather than powder formulations so as to provide lower resistance to air flow. At present, the preferred size of each of the components is nominally one eighth inch diameter particles i.e., particles of between 8 and 16 mesh. The zeolite particles are spherical in shape while the silica gel and activated carbon are essentially in chunk form (i.e., non-spherical or irregular shapes). The combination of chunk particle and spherical particles thus nestle together and completely fill the volume of the filter, keeping voids or open spaces to a minimum. Thus, the air to be filtered passes through each of the components as it passes through the thickness of the filter and thus removes the odors.

Also, for particular applications, it is possible to stack more than one filter element in the filter. For example, two filters spaced apart may be desirable for situations where an extremely high concentration of odors is present, to extend filter life.

The thickness and amount of filters is controlled by some extent to their replacement time. Advantageously, the system should be designed such that the filter requires replacement after a period of about six months to one year. Depending upon the exact amount and content of odors to be removed, it is possible that the filter element may have to be replaced on a monthly basis, although it is also possible that the filters can be useful for one year or longer in low odor containing air removal applications.

In accordance with another embodiment of the invention, the absorbent material for certain applications contains a liquid for inhibiting the growth of microorganisms. Those skilled in the art are well acquainted with liquids for inhibiting the growth of microorganisms. Preferred liquids include those having properties such as low vapor pressure, low irritation levels, low toxicity, more preferably, no toxicity, low chemical reactivity and high chemical stability. These liquids inhibit the growth of microorganisms in the filter and assist in deodorizing since certain odors are soluble in the liquids.

In accordance with the invention, a preferred liquid comprises a fungicide/bacteriocide preservative composition in an amount from about 0.5 to 2% by weight of the liquid, at least one polyhydric alcohol, the polyhydric alcohol being present in an amount from about 83 to 99.5% by weight of the liquid, and at least one additional compound for modifying the vapor pressure of the polyhydric alcohol, the additional compound being present in an amount from about 0 to 15% by weight of the liquid.

The fungicide/bacteriocide preservative composition is selected to prevent the growth of fungi and bacteria within the filter element itself. Preferred fungicide/bacteriocide preservative compositions include captan, quaternary ammonium cosmetic preservatives, parabens and iodophors.

Specifically preferred is captan (N-trichloromethyl thio-4-cyclohexene-1,2-dicarboximide, also know as N-trichloromethyl-thio-tetrahydrophthalimide) which has a molecular formula of $C_2H_8O_2NSCl_3$. A highly purified grade of captan is available from the R. T. Vanderbilt Company, Inc., 230 Park Avenue, New York, N.Y. 10017. This highly purified grade of captan, available in the form of a fine powder, has a Specific Gravity (average) of 1.7, a white to off-white color and a melting range of 171°–176° C.

Preferably, the fungicide/bacteriocide preservative composition is present in an amount of about 1% by weight of the liquid.

As defined herein, the polyhydric alcohol contains two or more hydroxyl groups. Included within this definition are compounds generally referred to as glycols, polyols and polyglycols.

A particularly preferred polyhydric alcohol is propylene glycol, which is defined herein to include 1,2-propylene glycol, 1,3-propylene glycol and a combination thereof. Further examples of suitable polyhydric alcohols include ethylene glycol, glycerin, polyethylene glycol, dipropylene glycol and other high boiling glycol ethers. Preferably, the polyhydric alcohol is non-toxic.

A preferred combination of polyhydric alcohol is propylene glycol and glycerin. Preferably, the propylene glycol is present in an amount from about 74 to 89% by weight of the liquid and the glycerin is present in an amount from about 5 to 10% by weight of the liquid. Most preferably, the glycerin is present in an amount of about 8.5% by weight of the liquid and the propylene glycol is present in an amount of about 80.5% by weight of the liquid.

An additional compound may be added to the liquid to modify the vapor pressure of the polyhydric alcohol. It is well-known that the vapor pressure of a liquid mixture having two ingredients is lower than the vapor pressure of the individual ingredients. Consequently, a combination of polyhydric alcohols modify the vapor pressure of each polyhydric alcohol in the combination.

Thus, if vapor pressure lowering is desired, a combination of polyhydric alcohols may be used and no additional compound need be added. If, however, only one polyhydric alcohol is used, or if a combination is used, but either case the vapor pressure is not low enough, an additional compound may be used to lower the vapor pressure as desired.

Those of ordinary skill in the art will readily be able to determine, without undue experimentation, suitable additional compounds for modifying the vapor pressure of the polyhydric alcohols. Preferably, these additional compounds include water or glycerine.

The amount of additional compound for modifying the vapor pressure of the polyhydric alcohol preferably ranges from about 5 to about 15% by weight based on the weight of the liquid. The most advantageous additional compound is water, present in an amount of about 10% by weight of the liquid.

Optionally, the liquid may also include other ingredients, such as perfumes, essential oils and the like, for imparting a pleasant odor or a medicinal effect to the treated air. In certain applications, it may be desirable to include an easily vaporized insecticide.

In accordance with the invention, the liquid may further include an oxidizing agent which is compatible with the liquid. A preferred oxidizing agent is a naringen-iron chelate produced from the reaction of naringen in an amount from about 0.1 to 0.2% by weight of the liquid with an iron salt in an amount of from about 0.01 to 0.10% by weight of the liquid.

Preferably, the iron salt is the commercially available form of ferric chloride hydrate. Most preferable, the naringen-iron chelate is produced from the reaction of naringen in an amount of 0.05 percent by weight of the liquid. The naringen-iron chelate is also effective in assisting in the removal of hydrogen sulfide from indoor air.

In accordance with another aspect of the invention, the liquid for inhibiting the growth of microorganisms may comprise the product obtained by contacting grapefruit pulp with a non-toxic polyhydric alcohol to form a reaction product, and separating the reaction product from the pulp residue. The method for making this specific liquid is described in U.S. Pat. No. 4,021,577, the disclosure of which is specifically incorporated herein by reference.

In accordance with the invention, this liquid for inhibiting the growth of microorganisms is also present in an amount of from 5 to about 50% by weight of the combined weight of the adsorbent and the liquid. Based on an amount of liquid by weight of the combined weight of the adsorbent and liquid, preferably the liquid is present in an amount of at least about 20%, and no more than about 45%. A preferred range is about 20 to 30%.

A further embodiment of the present invention relates to a filter element containing a first layer of silica gel which is impregnated with one of the above-described liquids for the prevention of growth of microorganisms, located adjacent to a second layer of zeolite, activated carbon and/or silica gel in a dry mixture. In this arrangement, it is possible for the first layer to be adjacent to the second layer in either a horizontal or vertical plane. The vertical arrangement is preferred, since the gas would have to pass through each layer and thus maximum removal of odors would be provided. It has also been found, however, that the filter is effective when the layers are adjacent to each other in a horizontal plane. In this regard, where a circular filter is used, two concentric adjacent areas of equal volume of absorbent can be used and one layer of either of the adsorbents can be placed in the first compartment and the other in the remaining compartment. Where a rectangular filter is used, it can be divided by a centrally located wall member, and equal amounts of volume of the filter placed in each compartment. As explained above, since the liquid is effective for preventing the growth of microorganisms, adsorbents containing the liquid it would be preferred for those indoor areas containing high levels of bacteria or other such microorganisms.

In another embodiment of the present invention, the filter element contains a layer of silica gel which is impregnated with the liquid as described above. The filter includes at least one layer of dry adsorbent components, such as mixture of silica gel, zeolite and/or activated carbon. Also, the zeolite, activated carbon and silica gel may all be intimately mixed and present in the second layer or the filter element may contain one or more layers containing only zeolite, one or more layers containing only activated carbon and one or more layers containing only silica gel, although this is not preferred due to the greater pressure drop through the filter.

As described above, where particulate matter is to be removed, the previously described combinations of high efficiency particulate removal paper and plastic foam can be used with the liquid impregnated adsorbents.

Without departing from the teachings of the invention, it is also possible to arrange various combinations of the above-described filter elements depending upon the particular odors to be encountered and removed.

EXAMPLES

The scope of the invention is further described in connection with the following examples which are set forth for purposes of illustration only and are not to be construed as limiting the scope of the invention in any manner.

The gas absorption measurements described in the Examples were conducted in an air chamber or by bench methods. For air chamber testing, the filter to be tested is placed in a 12 cubic foot sealed chamber connected to an infrared spectrophotometer equipped with a 20 meter gas measuring cell. The gas to be tested is introduced into the chamber. When the gas concentration is constant, the air treatment unit is activated and gas concentration versus time is measured. After a period of 1 hour, the gas remaining after passing through the filter is measured, and a removal efficiency is calculated.

It is necessary to calibrate the analytical instrument prior to each experiment. This is done by introducing quantities of the test chemical. Absorbance of infrared radiation is measured at a previously chosen wavelength. The result is a graph of light absorbance versus gas concentration at any time after the air treatment filter has been placed into the test system and activated.

In the preferred bench method, a quantity of gas absorbing medium is tested for ability to absorb a test gas and for capacity. The test gas (usually formaldehyde, ammonia, or hydrogen sulfide) is passed through a bed of the absorbant medium at a rate of about 10 cc/min. The concentration of the gas is measured by gas chromatography before it contacts the absorbant medium and again after passing through the medium.

EXAMPLE 1

To illustrate the effectiveness of known filtering media, separate filters made of active carbon, zeolite, and silica gel, respectively, were tested for removal of formaldehyde. Filters were tested in both the fresh (i.e., brand new) and aged condition. In the aged condition, the filters were left exposed to air for about 8 weeks. The removal efficiency of each filter was calculated after one hour. Results were as follows:

| Filter element | Removal efficiency % | |
|---|---|---|
| | fresh | aged |
| active carbon | 78.3 | 41.9 |
| zeolite | 97.2 | 76.1 |
| silica gel | 44.1 | 55.6 |

EXAMPLE 2

Next, the individual filters described above in Example 1 were each impregnated with a liquid to inhibit the growth of microorganisms. The liquid is the reaction product of grapefruit pulp and propylene glycol. The amount of liquid used is about 80% of the pore volume of the solid. These filter elements were then tested for formaldehyde removal in both the fresh and aged conditions.

| Filter element | Removal efficiency % | |
|---|---|---|
| | fresh | aged |
| active carbon/liquid | 99.9 | 87.4 |
| zeolite/liquid | 85.1 | 80.4 |
| silica gel/liquid | 84.7 | 78.9 |

This shows the beneficial effect of impregnating the dry component with the liquid. Liquid impregnated mixtures of these components as disclosed in applicant's parent applications, also produced improved removal efficiencies, as shown below.

| Filter element | Removal efficiency % | |
|---|---|---|
| | fresh | aged |
| 75% carbon/25% zeolite/liquid | 97.7 | 86.5 |
| 50% carbon/50% zeolite/liquid | 95.5 | 87.8 |
| 25% carbon/75% zeolite/liquid | 95.6 | 82.9 |

EXAMPLE 3

The filter elements according to the present invention were then made as follows:
formulation A: equal amounts of active carbon, zeolite, and silica gel (dry).
formulation B: a first layer of silica gel impregnated with the liquid of Example 2, and an adjacent second layer of equal amounts of active carbon and zeolite. The arrangement of the layers is as shown in FIG. 3.
These were tested in the aged condition for formaldehyde removal. Results were as follow:

| Filter element | Removal efficiency % aged |
|---|---|
| A | 87.2 |
| B | 80.7 |

EXAMPLE 4

The filter elements of Example 3 were then tested for ammonia removal. Results were as follows:

| Filter element | Removal efficiency % aged |
|---|---|
| A | 95.8 |
| B | 78.4 |

Thus clearly superior results are obtained with the filter elements of the present invention when used in the aged condition. Since these filters must be manufactured and then either placed in an air filter unit or shipped as replacement filters, there is a time delay from the time of manufacture and use. Thus, the filter elements of the present invention are preferred since they provide a high rate of removal even if not used immediately after manufacture.

While it is apparent that the invention herein disclosed is well calculated to fulfill the desired results, it will be appreciated that numerous modifications and embodiments may be devised by those skilled in the art, and it is intended that the appended claims cover all such modifications and embodiments as fall within the true spirit and scope of the present invention.

I claim:

1. An air filter element for removing odors from indoor air consisting essentially of a single layer of a dry mixture of silica gel, activated carbon and a zeolite.

2. The indoor air filter element according to claim 1 wherein said mixture comprises from about 10 to 80 weight percent of silica gel, from about 10 to 80 weight percent activated carbon, and from about 10 to 80 weight percent zeolite.

3. The indoor air filter element according to claim 1 wherein said amounts of silica gel, activated carbon, and zeolite are essentially equal.

4. The indoor air filter element according to claim 1 wherein said mixture contains a liquid for inhibiting the growth of microorganisms, said liquid comprising:
 (a) a fungicide/bacteriocide preservative composition in an amount from about 0.5 to 2% by weight of the liquid;
 (b) at least one polyhydric alcohol, said polyhydric alcohol being present in an amount from about 83 to 99.5% by weight of the liquid; and
 (c) at least one additional compound for modifying the vapor pressure of said polyhydric alcohol, said additional compound being present in an amount from about 0 to 15% by weight of the liquid, said liquid being present in an amount from about 5 to about 50% by weight of the combined weight of said mixture and said liquid.

5. The indoor air filter element according to claim 4 wherein said zeolite is zeolite X and said polyhydric alcohol is propylene glycol.

6. The indoor air filter element of claim 4 wherein said fungicide/bacteriocide preservative composition is captan, quaternary ammonium cosmetic preservatives, parabens, or iodophors.

7. The indoor air filter element of claim 6 wherein said fungicide/bacteriocide preservative composition is present in an amount of about 1% by weight of said liquid.

8. The indoor air filter element of claim 4 wherein said liquid further includes a naringen-iron chelate produced from the reaction of naringin in an amount from about 0.1 to 0.2% by weight of the liquid with an iron salt in an amount from about 0.01 to 0.10% by weight of the liquid.

9. The indoor air filter element of claim 4 wherein said polyhydric alcohol is a combination of propylene glycol, glycerin and tripropylene glycol and further wherein said additional compound is water or glycerine.

10. The indoor air filter element according to claim 1 wherein said mixture contains a liquid for inhibiting the growth of microorganisms, said liquid comprising the product obtained by contacting grapefruit pulp with a non-toxic polyhydric alcohol to form a reaction product, and separating said reaction product from the pulp residue, said liquid being present in an amount from about 5 to about 50% by weight of the combined weight of said mixture.

11. The indoor air filter element according to claim 10 wherein said zeolite is zeolite X and said polyhydric alcohol is propylene glycol.

12. The indoor air filter element of claim 10 wherein said liquid further includes a naringen-iron chelate produced from the reaction of naringen in an amount from about 0.1 to 0.2% by weight of the liquid with an iron salt in an amount from about 0.01 to 0.10% by weight of the liquid.

13. The indoor air filter element of claim 9 wherein said fungicide/bacteriocide preservative composition is present in an amount of about 1% by weight of said liquid.

14. An air filter element for removing odors from indoor air consisting essentially of:
   a. a first layer of silica gel impregnated with a liquid for inhibiting the growth of microorganisms, said liquid comprising:
      (i) a fungicide/bacteriocide preservative composition in an amount from about 0.5 to 2% by weight of the liquid;
      (ii) at least one polyhydric alcohol, said polyhydric alcohol being present in an amount from about 83 to 99.5% by weight of the liquid; and
      (iii) at least one additional compound for modifying the vapor pressure of said polyhydric alcohol, said additional compound being present in an amount from about 0 to 15% by weight of the liquid, said liquid being present in an amount from about 5 to about 50% by weight of the combined weight of said silica gel and said liquid, and
   b. a dry second layer of zeolite, active carbon, silica gel or mixtures thereof.

15. The indoor air filter element according to claim 14 wherein the weight of the silica gel in said first layer before impregnation with said liquid ranges from about 1:3 to 3:1 times the weight of the zeolite, active carbon, silica gel or mixtures thereof in said second layer.

16. The indoor air filter element according to claim 14 wherein the weight of silica gel in said first layer before impregnation with said liquid is essentially equal to the amount of zeolite, active carbon silica gel or mixtures thereof in said second layer.

17. The indoor air filter element according to claim 14 wherein said first and second layers are separated.

18. The indoor air filter element according to claim 14 wherein said first and second layers are adjacent in either a vertical or horizontal direction.

19. An air filter element for removing odors from indoor air consisting essentially of:
   a. a first layer of silica gel impregnated with a liquid for inhibiting the growth of microorganisms, said liquid comprising the product obtained by contacting grapefruit pulp with a non-toxic polyhydric alcohol to form a reaction product, and separating said reaction product from said pulp residue, said liquid being present in an amount from about 5 to 50% by weight of the combined weight of said silica gel and said liquid; and
   b. a dry second layer of zeolite, active carbon, silica gel or mixtures thereof.

20. The indoor air filter element according to claim 19 wherein the weight of the silica gel in said first layer before impregnation with said liquid ranges from about 1:3 to 3:1 times the weight of the zeolite, active carbon, silica gel or mixtures thereof in said second layer.

21. The indoor air filter element according to claim 19 wherein the weight of silica gel in said first layer before impregnation with said liquid is essentially equal to the amount of zeolite, active carbon, silica gel or mixtures thereof in said second layer.

22. The indoor air filter element according to claim 19 wherein said first and second layers are separated.

23. The indoor air filter element according to claim 19 wherein said first and second layers are adjacent in either a vertical or horizontal direction.

24. An air filter element for removing odors and particulate matter from indoor air comprising:
   (a) a first layer of the air filter element according to claim 1;
   (b) at least one layer of particulate removal means located adjacent to said first layer.

25. The indoor air filter element according to claim 24 wherein said particulate removal means is paper, felt, fabric, fiberglass, or plastic foam.

26. The indoor air filter of claim 25 wherein said plastic foam is polyurethane containing 20 pores per inch.

27. The indoor air filter of claim 25 wherein said paper is high efficiency air filter paper.

28. The indoor air filter element according to claim 24 wherein two layers of particulate removal means, one layer located on each side adjacent said first layer, are used.

29. An air filter element for removing odors and particulate matter from indoor air comprising:
   (a) a first layer of the air filter element according to claim 4;
   (b) at least one layer of particulate removal means located adjacent to said first layer.

30. An air filter element for removing odors and particulate matter from indoor air comprising:
   (a) a first layer of the air filter element according to claim 10;
   (b) at least one layer of particulate removal means located adjacent to said first layer.

31. An air filter element for removing odors and particulate matter from indoor air comprising:

(a) a first layer of the air filter element according to claim 14;
(b) at least one layer of particulate removal means located adjacent to said first layer.

32. An air filter element for removing odors and particulate matter from indoor air comprising:
   (a) a first layer of the air filter element according to claim 19;
   (b) at least one layer of particulate removal means located adjacent to said first layer.

33. An air treatment filter for removing odors and particulate matter from indoor air comprising:
   (a) housing means;
   (b) at least one filter element according to claim 24;
   (c) support means for holding the at least one filter element within the housing means; and
   (d) fan means for directing indoor air into said housing and through said filter element.

34. An air treatment filter for removing odors and particulate matter from indoor air comprising:
   (a) housing means;
   (b) at least one filter element according to claim 29;
   (c) support means for holding the at least one filter element within the housing means; and
   (d) fan means for directing indoor air into said housing and through said filter element.

35. An air treatment filter for removing odors and particulate matter from indoor air comprising:
   (a) housing means;
   (b) at least one filter element according to claim 30;
   (c) support means for holding the at least one filter element within the housing means; and
   (d) fan means for directing indoor air into said housing and through said filter element.

36. An air treatment filter for removing odors and particulate matter from indoor air comprising:
   (a) housing means;
   (b) at least one filter element according to claim 31;
   (c) support means for holding the at least one filter element within the housing means, and
   (d) fan means for directing indoor air into said housing and through said filter element.

37. An air treatment filter for removing odors and particulate matter from indoor air comprising:
   (a) housing means;
   (b) at least one filter element according to claim 32;
   (c) support means for holding the at least one filter element within the housing means; and
   (d) fan means for directing indoor air into said housing and through said filter element.

38. A method for removing odors and particulate matter from indoor air which comprises directing said indoor air through the indoor air filter of claim 33.

39. A method for removing odors and particulate matter from indoor air which comprises directing said indoor air through the indoor air filter of claim 34.

40. A method for removing odors and particulate matter from indoor air which comprises directing said indoor air through the indoor air filter of claim 35.

41. A method for removing odors and particulate matter from indoor air which comprises directing said indoor air through the indoor air filter of claim 36.

42. A method for removing odors and particulate matter from indoor air which comprises directing said indoor air through the indoor air filter of claim 37.

* * * * *